US 6,458,822 B2

(12) United States Patent
Robinson et al.

(10) Patent No.: US 6,458,822 B2
(45) Date of Patent: Oct. 1, 2002

(54) 2-OXO-IMIDAZOLIDINE-4-CARBOXYLIC ACID HYDROXAMIDE COMPOUNDS THAT INHIBIT MATRIX METALLOPROTEINASES

(75) Inventors: Ralph P. Robinson, Gales Ferry; Ellen R. Laird, Mystic, both of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/730,302

(22) Filed: Dec. 5, 2000

Related U.S. Application Data

(60) Provisional application No. 60/188,892, filed on Mar. 13, 2000.

(51) Int. Cl.$^7$ .................. A61K 31/4166; C07D 233/02
(52) U.S. Cl. ..................................... 514/401; 548/333.5
(58) Field of Search ....................... 548/333.5; 514/385, 514/386, 399, 400, 401

(56) References Cited

U.S. PATENT DOCUMENTS

| | | |
|---|---|---|
| 5,763,469 A | 6/1998 | Delucca |
| 5,861,510 A | 1/1999 | Piscopio et al. |
| 6,118,016 A | 9/2000 | Hawkins |

FOREIGN PATENT DOCUMENTS

| | | |
|---|---|---|
| EP | 0606046 A1 | 7/1994 |
| EP | 0606046 B1 | 10/1997 |
| EP | 0935963 A2 | 8/1999 |
| EP | 0949244 A2 | 10/1999 |
| EP | 0949245 A1 | 10/1999 |
| EP | 1004578 A | 5/2000 |
| WO | WO 96/27583 | 9/1996 |
| WO | WO 98/03516 | 1/1998 |
| WO | WO 98/07697 | 2/1998 |
| WO | WO 98/08815 | 3/1998 |
| WO | WO 98/08825 | 3/1998 |
| WO | WO 98/34918 | 8/1998 |
| WO | WO 98/37768 | 9/1998 |
| WO | WO99/65867 | 12/1999 |
| WO | WO 00/09492 | 2/2000 |

OTHER PUBLICATIONS

Caplus 121:274211 (English Abstract) Szarapinska–Kwaszewska 1994, vol. 46, Issue 1–2, pp. 25–27.*
Caplus 135:152749 (English Abstract) Robinson et al 2001, vol. 11, issue 9 pp. 1211–1213.*
N. Rawlings, et al., "Evolutionary Families of Metallopeptidases", in *Methods in Enzymology*, 248, Chapter 13, pp. 183–228, (1995).
W. Stocker, et al., "The metzincins—Topological and sequential relations between the astacins, adamalysins, serralysins, and matrixins (collagenases) define a superfamily of zinc–peptidases", *Protein Science*, 4, pp. 823–840, (1995).

P. Mitchell, et al., "Cloning, Expression, and Type II Collagenolytic Activity of Matrix Metalloproteinase–13 from Human Osteoarthritic Cartilage", *J. Clin. Invest.*, 97, 761–768, (1996).

T. Wolfsberg, et al., ADAM, a Novel Family of Membrane Proteins Containing a Disintegrin And Metalloprotease Domain: Multipotential Functions in Cell–Cell and CellMatrix Interactions, in *J. Cell Biol.*, 131, pp. 275–278, (1995).

W. Friers, "Tumor necrosis factor, Characterization at the molecular, cellular and in vivo level" *FEBS Letters*, 285, pp. 199–212, (1991).

C. Spooner, et al., "The Role of Tumor Necrosis Factor in Sepsis", *Clinical Immunology and Immunopathology*, pp. S11–S17, Academic Press, Inc., 1992.

K. Kuno, et al., "Molecular Cloning of a Gene Encoding a New Type of Metalloproteinase–disintegrin Family Protein with Thrombospondin Motifs as an Inflammation Associated Gene", *J. Biol. Chem.*, 272, pp. 556–562, 1997.

E. Wu, et al., Expression of Members of the Novel Membrane Linked Metalloproteinase Family ADAM in Cells Derived from a Range of Haematological Malignancies, in *Biochem. Biophys. Res. Comm.*, 235, pp. 437–442, 1997.

* cited by examiner

*Primary Examiner*—Alan L. Rotman
*Assistant Examiner*—Rita Desai
(74) *Attorney, Agent, or Firm*—Peter C. Richardson; Paul H. Ginsburg; E. Victor Donahue

(57) ABSTRACT

The present invention relates to a compound of the formula (I)

wherein $R^1$, $R^2$, $R^3$ and $R^4$ are as defined above, and pharmaceutically acceptable salts and solvates thereof, that are useful, for example, as matrix metalloproteinase inhibitors. The present invention is also directed to pharmaceutical compositions comprising such compounds and methods of treatment for diseases such as osteoarthritis, rheumatoid arthritis, cancer, osteoporosis, tissue ulceration, restinosis, periodontal disease, inflammation, epidermolysis bullosa, scleritis, stroke, Alzheimer's disease, and the like, characterized by inappropriate matrix metalloproteinase activity. Processes for the synthesis of compounds of formula (I) are also disclosed.

27 Claims, No Drawings

2-OXO-IMIDAZOLIDINE-4-CARBOXYLIC ACID HYDROXAMIDE COMPOUNDS THAT INHIBIT MATRIX METALLOPROTEINASES

The present application claims priority under 35 USC section 119(e) to U.S. provisional application No. 60/188,892, filed Mar. 13, 2000, the complete text and claims of which are incorporated by reference herein as if fully set forth.

BACKGROUND OF THE INVENTION

The present invention relates to 2-oxo-imidazolidine-4-carboxylic acid hydroxamide derivatives, and to pharmaceutical compositions comprising such derivatives, and to the use of such derivatives in the treatment of arthritis, inflammation, cancer, and other diseases as described below.

The compounds of the present invention are inhibitors of zinc metalloendopeptidases, especially those belonging to the matrix metalloproteinase (also called MMP or matrixin) and reprolysin (also known as adamylsin) subfamilies of the metzincins (Rawlings, et al., *Methods in Enzymology*, 248, 183–228 (1995) and Stocker, et al., *Protein Science*, 4, 823–840 (1995)).

The MMP subfamily of enzymes, currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMP's are most well known for their role in regulating the turn-over of extracellular matrix proteins and as such play important roles in normal physiological processes such as reproduction, development and differentiation. In addition, the MMP's are expressed in many pathological situations in which abnormal connective tissue turnover is occurring. For example, MMP-13, an enzyme with potent activity at degrading type II collagen (the principal collagen in cartilage), has been demonstrated to be overexpressed in osteoarthritic cartilage (Mitchell, et al., *J. Clin. Invest.*, 97, 761 (1996)). Other MMPs (MMP-2, MMP-3, MMP-8, MMP-9, MMP-12) are also overexpressed in osteoarthritic cartilage and inhibition of some or all of these MMP's is expected to slow or block the accelerated loss of cartilage typical of joint diseases such as osteoarthritis or rheumatoid arthritis.

Overexpression of certain metalloproteinases is also associated with metastasis of tumor cells. It is believed that such activity is essential to the invasion of healthy tissues. Inhibition of the activity of some or all of these proteinases is expected to limit the spread of malignant cells. Additionally, certain metalloproteinases are necessary for angiogenesis, the process whereby, for example, a growing tumor obtains additional blood supply through new vascularization. Therefore inhibition of these enzymes is expected to slow or arrest tumor growth.

The compounds of the invention are also expected to usefully inhibit additional classes of enzymes having important roles in both normal and pathological processes. For example, the mammalian reprolysins are known as ADAMs (A Disintegrin And Metalloproteinase) (Wolfberg, et al., *J. Cell Biol.*, 131, 275–278 (1995)) and contain a disintegrin domain in addition to a metalloproteinase-like domain. To date, twenty three distinct ADAM's have been identified. ADAM-17, also known as tumor necrosis factor-alpha converting enzyme (TACE), is the most well known ADAM.

ADAM-17 (TACE) is responsible for cleavage of cell bound tumor necrosis factor-alpha (TNF-α, also known as cachectin). TNF-α is recognized to be involved in many infectious and auto-immune diseases (W. Friers, *FEBS Letters*, 285, 199 (1991)). Furthermore, it has been shown that TNF-α is the prime mediator of the inflammatory response seen in sepsis and septic shock (Spooner, et al., *Clinical Immunology and Immunopathology*, 62 S11 (1992)). There are two forms of TNF-α, a type II membrane protein of relative molecular mass 26,000 (26 kD) and a soluble 17 kD form generated from the cell bound protein by specific proteolytic cleavage. The soluble 17 kD form of TNF-α is released by the cell and is associated with the deleterious effects of TNF-α. This form of TNF-α is also capable of acting at sites distant from the site of synthesis. Thus, inhibitors of TACE prevent the formation of soluble TNF-α and prevent the deleterious effects of the soluble factor.

In a further example, aggrecanase, is an enzyme that is important in the degradation of cartilage aggrecan. Aggrecanase is believed to be an ADAM. The loss of aggrecan from the cartilage matrix is an important factor in the progression of joint diseases such as osteoarthritis and rheumatoid arthritis and inhibition of aggrecanase is expected to slow or block the loss of cartilage in tissues affected by these diseases.

Other ADAMs that have shown expression in pathological situations include ADAM TS-1 (Kuno, et al., *J. Biol. Chem.*, 272, 556–562 (1997)), and ADAM's 10, 12 and 15 (Wu, et al., *Biochem. Biophys. Res. Comm.*, 235, 437–442, (1997)). As knowledge of the expression, physiological substrates and disease association of the ADAM's increases the full significance of the role of inhibition of this class of enzymes will be appreciated.

The compounds of the invention are useful in the treatment of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, inflammation, allergic contact hypersensitivity, cancer (such as solid tumor cancer including colon cancer, breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis or septic shock.

The compounds of the present invention are also useful in the treatment of diseases in which inhibition of MMP's and/or ADAM's will provide therapeutic benefit, such as those characterized by matrix metalloproteinase or ADAM expression.

Matrix metalloproteinase and reprolysin inhibitors are well known in the literature. Specifically, European Patent Publication 606,046, published Jul. 13, 1994 refers to ceratin heterocyclic MMP inhibitors. PCT Publication WO 98/08825 and WO 98/08815, both published Mar. 5, 1998, refer to certain cyclic hydroxamic acid MMP inhibitors. U.S. Pat. No. 5,861,510, issued Jan. 19, 1999, refers to cyclic arylsulfonylamino hydroxamic acids that are useful as MMP inhibitors. PCT Publication WO 98/34918, published Aug. 13, 1998, refers to cyclic hydroxamic acids including certain dialkyl substituted compounds that are useful as MMP inhibitors.

PCT publications WO 96/27583 and WO 98/07697, published Mar. 7, 1996 and Feb. 26, 1998, respectively, refer to arylsulfonyl hydroxamic acids. PCT publication WO 98/03516, published Jan. 29, 1998, refers to phosphinates with MMP activity. PCT publication 98/33768, published Aug. 6, 1998, refers to N-unsubstituted arylsulfonylamino hydroxamic acids. European Patent Publication EP 935,963, published Aug. 18, 1999 refers to the use of MMP-13 selective inhibitors for the treatment of osteoarthritis. U.S. patent applications Ser. No. 09/290,022 09/287,930 and 09/287,508 filed Apr. 9, 1999, Apr. 7, 1999 and April 7, 1999 respectively, refer to methods of preparing hydroxamic acids. United States Provisional Patent Application entitled "Selective Inhibitors of Aggecanase in Osteoarthritis Treatment," filed Aug. 12, 1999 refers to MMP, Aggrecanase and TACE inhibitors and to additional methods of preparing hydroxamic acids. United States Non-Provisional Application entitled "TACE Inhibitors," filed Aug. 12, 1999, refers to heterocyclic hydroxamic acids. Each of the above referenced publications and applications is hereby incorporated by reference in its entirety.

It is recognized that different combinations of MMP's and ADAM's are expressed in different pathological situations. As such, inhibitors with specific selectivities for individual ADAM's and/or MMP's may be preferred for individual diseases. For example, rheumatoid arthritis is an inflammatory joint disease characterized by excessive TNF levels and the loss of joint matrix constituents. In this case, a compound that inhibits TACE and aggrecanase as well as MMP's such as MMP-13 may be the preferred therapy. In contrast, in a less inflammatory joint disease such as osteoarthritis, compounds that inhibit matrix degrading MMP's such as MMP-13 but not TACE may be preferred.

SUMMARY OF THE INVENTION

The present invention relates to a compound according to formula (I)

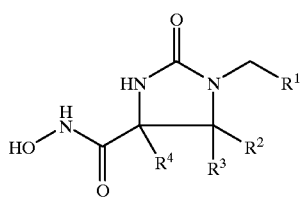

(I)

or a pharmaceutically acceptable salt or solvate thereof, wherein $R^1$ is selected from the groups consisting of $(C_6-C_{10})$aryl, $(C_1-C_9)$heteroaryl, $(C_6-C_{10})$aryl$(C_1-C_6)$alkyl, $(C_1-C_9)$heteroaryl$(C_1-C_6)$alkyl, $(C_6-C_{10})$aryl$(C_6-C_{10})$aryl, $(C_1-C_9)$heteroaryl$(C_6-C_{10})$aryl, $(C_6-C_{10})$aryl$(C_1-C_9)$heteroaryl, $(C_1-C_9)$heteroaryl$(C_1-C_9)$heteroaryl, $(C_6-C_{10})$aryloxy$(C_6-C_{10})$aryl, $(C_1-C_9)$heteroaryloxy$(C_6-C_{10})$aryl, $(C_6-C_{10})$aryloxy$(C_1-C_9)$heteroaryl, $(C_1-C_9)$heteroaryloxy$(C_1-C_9)$heteroaryl, $(C_6-C_{10})$aryloxy$(C_1-C_6)$alkyl, $(C_1-C_9)$heteroaryloxy $(C_1-C_6)$alkyl, $(C_6-C_{10})$aryl$(C_1-C_6)$alkyl$(C_6-C_{10})$aryl, $(C_1-C_9)$heteroaryl$(C_1-C_6)$alkyl$(C_6-C_{10})$aryl, $(C_6-C_{10})$aryl$(C_1-C_6)$alkyl$(C_1-C_9)$heteroaryl, $(C_1-C_9)$heteroaryl $(C_1-C_6)$alkyl$(C_1-C_9)$ heteroaryl, $(C_6-C_{10})$aryl$(C_1-C_6)$ alkoxy$(C_6-C_{10})$aryl, $(C_1-C_9)$heteroaryl$(C_1-C_6)$alkoxy $(C_6-C_{10})$aryl, $(C_6-C_{10})$aryl$(C_1-C_6)$alkoxy$(C_1-C_9)$ heteroaryl, $(C_1-C_9)$heteroaryl$(C_1-C_6)$alkoxy$(C_1-C_9)$ heteroaryl, $(C_6-C_{10})$aryloxy$(C_1-C_6)$alkyl$(C_6-C_{10})$aryl, $(C_1-C_9)$heteroaryloxy$(C_1-C_6)$alkyl$(C_6-C_{10})$aryl, $(C_6-C_{10})$aryloxy$(C_1-C_6)$alkyl$(C_1-C_9)$heteroaryl, $(C_1-C_9)$heteroaryloxy$(C_1-C_6)$alkyl$(C_1-C_9)$heteroaryl, $(C_6-C_{10})$aryl$(C_6-C_{10})$aryl$(C_1-C_6)$alkyl, $(C_1-C_9)$ heteroaryl$(C_6-C_{10})$aryl$(C_1-C_6)$alkyl, $(C_6-C_{10})$ heteroaryl$(C_1-C_6)$alkyl, $(C_1-C_9)$heteroaryl$(C_1-C_9)$ heteroaryl$(C_1-C_6)$alkyl, $(C_6-C_{10})$aryl$(C_1-C_6)$alkoxy $(C_1-C_6)$alkyl, and $(C_1-C_9)$heteroaryl$(C_1-C_6)$alkoxy $(C_1-C_6)$alkyl, wherein, independently, each of the ring carbon atoms of said $(C_6-C_{10})$aryl and $(C_1-C_9)$heteroaryl moieties that is capable of forming an additional bond is optionally substituted by a group selected from fluoro, chloro, bromo, $(C_1-C_6)$alkyl, $(C_1-C_6)$alkoxy, perfluoro $(C_1-C_3)$alkyl, and perfluoro$(C_1-C_3)$alkoxy;

$R^2$ and $R^3$ are each independently selected from hydrogen and $(C_1-C_6)$alkyl, or taken together form a spiro ring of the formula

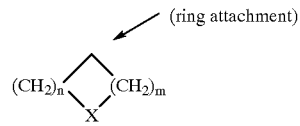

wherein X is a bond, $CH_2$, O, S, NH or $N(C_1-C_6)$alkyl, n is independently 1 or 2, and m is independently 1 or 2; and $R^4$ is hydrogen or $(C_1-C_6)$alkyl.

In a preferred aspect of the invention, $R^1$ is selected from the group consisting of $(C_6-C_{10})$aryl, $(C_1-C_9)$heteroaryl, $(C_6-C_{10})$aryloxy$(C_6-C_{10})$aryl, $(C_1-C_9)$heteroaryloxy $(C_6-C_{10})$aryl, $(C_6-C_{10})$aryl$(C_6-C_{10})$aryl, $(C_1-C_9)$heteroaryl $(C_6-C_{10})$aryl, $(C_6-C_{10})$aryl$(C_1-C_6)$alkoxy$(C_6-C_{10})$aryl, and $(C_1-C_9)$heteroaryl$(C_1-C_6)$alkoxy$(C_6-C_{10})$aryl.

In further preferred aspects of the invention, $R^1$ is selected:

(a) from the group consisting of 4-[$(C_6-C_{10})$aryl]phenyl, 4-[$(C_6-C_{10})$aryloxy]phenyl and 4-[$(C_6-C_{10})$aryl $(C_1-C_6)$alkoxy]phenyl; or (b) from the group consisting of 4-[$(C_1-C_9)$heteroaryl] phenyl, 4-[$(C_1-C_9)$heteroaryloxy]phenyl and 4-[$(C_1-C_9)$heteroaryl$(C_1-C_6)$alkoxy]phenyl.

Highly preferred examples include those wherein $R^1$ is 4-(4-fluorophenoxy)phenyl, 4-(4-chlorophenoxy)phenyl and 4-(naphthalen-2-yloxy)phenyl.

In a preferred aspect of the invention $R^2$ and $R^3$ taken together form a spiro ring of theformula

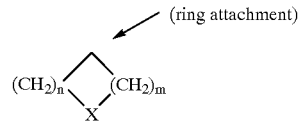

wherein X is a bond, $CH_2$, O, S, NH or $N(C_1-C_6)$alkyl, n is 1 or 2, and m is 1 or 2, such that n is the same as m.

In a further preferred aspect of the invention, $R^2$ and $R^3$ are selected from hydrogen and $(C_1-C_6)$alkyl. According to this aspect of the invention, it is preferred that $R^2$ be the same as $R^3$, that is, $R^2$ and $R^3$ are each hydrogen, or are each $(C_1-C_6)$alkyl, such that $R^2$ is the same as $R^3$ In preferred examples of the invention $R^4$ is $(C_1-C_6)$alkyl; $R^4$ is hydrogen; and $R^2$, $R^3$ and $R^4$ are each hydrogen.

In a highly preferred embodiment of the invention, the ring carbon to which $R^4$ attaches possesses the R configuration. Accordingly, preferred compounds of the invention are provided according to the formula (I')

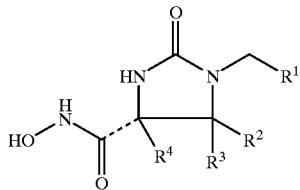

(I')

wherein the preference in selection of groups $R^1$, $R^2$, $R^3$ and $R^4$ is as aforementioned with respect to compounds wherein stereospecific configuration is unspecified at the ring carbon atom to which $R^4$ attaches.

Accordingly, preferred compounds of the invention include (4R)-1-[4-(4-Fluorophenoxy)benzyl]-2-oxo-imidazolidine-4-carboxylic acid hydroxyamide;

(4R)-1-[4-(Naphthalen-1-yloxy)benzyl]-2-oxo-imidazolidine-4-carboxylic acid hydroxyamide;

(4R)-1-[4-(Naphthalen-2-yloxy)benzyl]-2-oxo-imidazolidine-4-carboxylic acid hydroxyamide;

(4R)-1-(4-Methoxybenzyl)-2-oxo-imidazolidine-4-carboxylic acid hydroxyamide;

(4R)-1-[3-(4-Fluorophenoxy)benzyl]-2-oxo-imidazolidine-4-carboxylic acid hydroxyamide;

(4R)-1-Naphthalen-2-ylmethyl-2-oxo-imidazolidine-4-carboxylic acid hydroxyamide;

(4R)-1-(4-Fluorobiphenyl-4-ylmethyl)-2-oxo-imidazolidine-4-carboxylic acid hydroxyamide;

(4R)-1-(4-Benzyloxybenzyl)-2-oxo-imidazolidine-4-carboxylic acid hydroxyamide; and (4R)-1-[4-(2–Chloro-4-fluorobenzyloxy)benzyl]-2-oxo-imidazolidine-4-carboxylic acid hydroxyamide;

Additional preferred compounds of the invention include:

(4R)-1-[4-(4-Chlorophenoxy)benzyl]-2-oxo-imidazolidine-4-carboxylic acid hydroxyamide;

(4R)-1-[4-(4-Fluorophenoxy)benzyl]-2-oxo-7-oxa-1,3-diazaspiro[4.4]nonane-4-carboxylic acid hydroxyamide;

(4R)-2-Oxo-1-[4-(pyridin-4-yloxy)benzyl]imidazolidine-4-carboxylic acid hydroxyamide;

(4R)-4-Methyl-2-oxo-1-[4-(pyridin-4-yloxy)benzyl] imidazolidine-4-carboxylic acid hydroxyamide;

(4R)-5,5-Dimethyl-2-oxo-1-[4-(pyridin-4-yloxy)benzyl] imidazolidine-4-carboxylic acid hydroxyamide;

(4R)-1-[4-(4-Fluorophenoxy)benzyl]-5,5-dimethyl-2-oxo-imidazolidine-4-carboxylic acid hydroxyamide;

(4R)-1-[4-(4-Chlorophenoxy)benzyl]-5,5-dimethyl-2-oxo-imidazolidine-4-carboxylic acid hydroxyamide;

(4R)-1-[4-(4-Fluorophenoxy)benzyl]-4-methyl-2-oxo-imidazolidine-4-carboxylic acid hydroxyamide;

(4R)-1-[4-(4-Chlorophenoxy)benzyl]-4-methyl-2-oxo-imidazolidine-4-carboxylic acid hydroxyamide;

(4R)-1-[4-(4-Fluorophenoxy)benzyl]-2-oxo-1,3-diazaspiro[4.4]nonane-4-carboxylic acid hydroxyamide;

(4R)-1-[4-(4-Chlorophenoxy)benzyl]-2-oxo-1,3-diazaspiro[4.4]nonane-4-carboxylic acid hydroxyamide;

(4R)-1-[4-(4-Fluorophenoxy)benzyl]-4,5,5-trimethyl-2-oxo-imidazolidine-4-carboxylic acid hydroxyamide;

(4R)-1-[4-(4-Chlorophenoxy)benzyl]-4,5,5-trimethyl-2-oxo-imidazolidine-4-carboxylic acid hydroxyamide;

(4R)-4-Methyl-1-[4-(naphthalen-2-yloxy)benzyl]-2-oxo-imidazolidine-4-carboxylic acid hydroxyamide;

(4R)-5,5-Dimethyl-1-[4-(naphthalen-2-yloxy)benzyl]-2-oxo-imidazolidine-4-carboxylic acid hydroxyamide;

(4R)-1-[4-(5-Fluoropyridin-2-yloxy)benzyl]-4-methyl-2-oxo-imidazolidine-4-carboxylic acid hydroxyamide;

(4R)-2-Oxo-1-(4-pyridin-4-ylbenzyl)imidazolidine-4-carboxylic acid hydroxyamide and (4R)-2-Oxo-1-(4-pyridylmethyl)imidazolidine-4-carboxylic acid hydroxyamide.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is as defined above.

The term "aryl" as used herein, unless otherwise indicated, includes an organic radical derived from a monocyclic or bicyclic $(C_6-C_{10})$ aromatic hydrocarbon by removal of one hydrogen, such as phenyl or naphthyl, optionally substituted by substituents selected from the group consisting of fluoro, chloro, bromo, perfluoro$(C_1-C_6)$alkyl (including trifluoromethyl), $(C_1-C_6)$alkoxy, perfluoro $(C_1-C_3)$alkoxy (including trifluoromethoxy and difluoromethoxy) and $(C_1-C_6)$alkyl. Unless otherwise indicated, selection of each optional substituent is independent of selection of any other optional substituents, and perferably the number of substituents is zero, or is between 1 and 3.

The term "heteroaryl" as used herein, unless otherwise indicated, includes an organic radical derived from a monocyclic or bicyclic $(C_1-C_9)$ aromatic heterocyclic compound by removal of one hydrogen, such as pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl and benzoxazolyl, optionally substituted by substituents selected from the group consisting of fluoro, chloro, trifluoromethyl, $(C_1-C_6)$alkoxy, trifluoromethoxy, difluoromethoxy and $(C_1-C_6)$alkyl. Unless otherwise indicated, selection of each optional substituent is independent of selection of any other optional substituents, and preferably the number of substituents is zero, or is between 1 and 2. "A suitable substituenr" is intended to mean a chemically and pharmaceutically acceptable functional group i.e., a moiety that does not substantially negate the inhibitory activity of the inventive compounds, and/or a moiety that contributes properties useful to production, storage, or use of the inventive compounds as pharmaceuticals. Such suitable substituents may be determined by those skilled in the art. Illustrative examples of suitable substituents include, but are not limited to, alkyl groups, hydroxy groups, alkylthio groups, alkoxy groups, groups, carboxy groups, amino groups, alkyl- and dialkylamino groups, carbamoyl groups, alkylcarbonyl groups, alkoxycarbonyl groups, alkylaminocarbonyl groups dialkyamino carbonyl groups, arylcarbonyl groups, aryloxycarbonyl groups, alkylsulfonyl groups, an arylsulfonyl groups and the like.

The compound of formula I may have chiral centers and therefore exist in different enantiomeric forms. This invention relates to all optical isomers, tautomers and stereoisomers of the compounds of formula I and mixtures thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg., calcium and magnesium), ammonium or water-soluble amine addition salts such as N-methylglucamine-(meglumine), and the lower alkanolammonium and other base salts of pharmaceutically acceptable organic amines.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

The present invention also relates to a pharmaceutical composition for the treatment of a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer (such as solid tumor cancer including colon cancer breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising an amount of a compound of formula I or a pharmaceutically acceptable salt thereof effective in such treatments and a pharmaceutically acceptable carrier.

The present invention also relates to a pharmaceutical composition for the treatment of diseases characterized by metalloproteinase activity (preferably MMP-13) and other diseases characterized by mammalian reprolysin activity (preferably Aggrecanase activity most preferably Aggrecanase activity) in a mammal, including a human, comprising an amount of a compound of formula I or a pharmaceutically acceptable salt thereof effective in such treatments and a pharmaceutically acceptable carrier.

The present invention also relates to a pharmaceutical composition for the inhibition of (a) matrix metalloproteinases or other metalloproteinases involved in matrix degradation, or (b) a mammalian reprolysin (such as aggrecanase or ADAM's TS-1, 10, 12, 15 and 17, most preferably Aggrecanase) in a mammal, including a human, comprising an effective amount of a compound of formula I or a pharmaceutically acceptable salt thereof and a pharmaceutically acceptable carrier.

The present invention also relates to a method for treating a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, inflammation, cancer (such as solid tumor cancer including colon cancer breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising administering to said mammal an amount of a compound of formula I or a pharmaceutically acceptable salt thereof effective in treating such a condition.

The present invention also relates to the treatment of diseases characterized by matrix metalloproteinase activity (preferably MMP-13 activity) and other diseases characterized by mammalian reprolysin activity (preferably Aggrecanase activity) in a mammal, including a human, comprising administering to said mammal an amount of a compound of formula I or a pharmaceutically acceptable salt thereof effective in treating such a condition.

The present invention also relates to a method for the inhibition of (a) matrix metalloproteinases or other metalloproteinases involved in matrix degradation, or (b) a mammalian reprolysin (such as aggrecanase or ADAM's TS-1, 10, 12, 15 and 17, preferably Aggrecanase) in a mammal, including a human, comprising administering to said mammal an effective amount of a compound of formula I or a pharmaceutically acceptable salt thereof.

The present invention also relates to a method of inhibiting the cleavage of TNF-α from cell membranes in a mammal comprising administering to such mammal an effective amount of compound of formula I that inhibits Aggrecanase.

The present invention also relates to a method of treating arthritis in a mammal, comprising administering to such mammal an effective amount of an Aggrecanase inhibitor, wherein said Aggrecanase inhibitor selectively inhibits Aggrecanase in preference to MMP-1.

The present invention also relates to a method of treating arthritis in a mammal, comprising administering to such mammal an effective amount of an Aggrecanase inhibitor, wherein said Aggrecanase inhibitor selectively inhibits Aggrecanase at least ten times as well as MMP-1.

The present invention also relates to a method of treating arthritis in a mammal, comprising administering to such mammal an effective amount of an Aggrecanase inhibitor, wherein said Aggrecanase inhibitor selectively inhibits Aggrecanase and MMP-13 in preference to MMP-1.

The present invention also relates to a method of treating arthritis in a mammal, comprising administering to such mammal an effective amount of an Aggrecanase inhibitor, wherein said Aggrecanase inhibitor selectively inhibits Aggrecanase and MMP-13 at least ten times as well as MMP-1.

The present invention also relates to a method of treating arthritis in a mammal, comprising administering to such mammal an effective amount of a hydroxamic acid Aggrecanase inhibitor, wherein said Aggrecanase inhibitor selectively inhibits Aggrecanase and MMP-13 in preference to MMP-1.

The present invention also relates to a method of treating arthritis in a mammal, comprising administering to such mammal an effective amount of a hydroxamic acid Aggrecanase inhibitor, wherein said Aggrecanase inhibitor selectively inhibits Aggrecanase and MMP-13 at least ten times as well as MMP-1.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

This invention also encompasses pharmaceutical compositions containing prodrugs of compounds of the formula I.

This invention also encompasses methods of treating or preventing disorders that can be treated or prevented by the inhibition of matrix metalloproteinases or the inhibition of mammalian reprolysin comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TACE inhibitors, TNF-α inhibitors such as anti-TNF monoclonal antibodies and TNF receptor immunoglobulin molecules (such as Enbrel®), COX-2 inhibitors low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, requip, miratex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, droloxifene or fosomax and immunosuppressant agents such as FK-506 and rapamycin.

DETAILED DESCRIPTION OF THE INVENTION

The following reaction schemes illustrates the preparation of the compounds of the present invention. Unless otherwise indicated, $R^1$, $R^2$, and $R^3$ and $R^4$ in the reaction schemes and the discussion that follows are defined as above.

tert-butyl, benzyl, 2-trimethylsilylethyl or allyl. The preferred protecting group is 2-trimethylsilylethyl. When $p^2$ is benzyl, removal of the hydroxyamide protecting group is carried out by hydrogenolysis using catalytic palladium on barium sulfate in a polar solvent such as methanol at a temperature of about 20° C. When $p^2$ is 2-trimethylsilylethyl, removal of the hydroxyamide protecting group is carried out using boron trifluoride etherate in an inert solvent such as methylene chloride or chloroform, preferably methylene chloride, at a temperature from about 0° C. to about 50° C., preferably about 20° C. When $p^3$ is tert-butyl, removal of the protecting group is performed using a strong acid such as trifluoroacetic acid in an inert

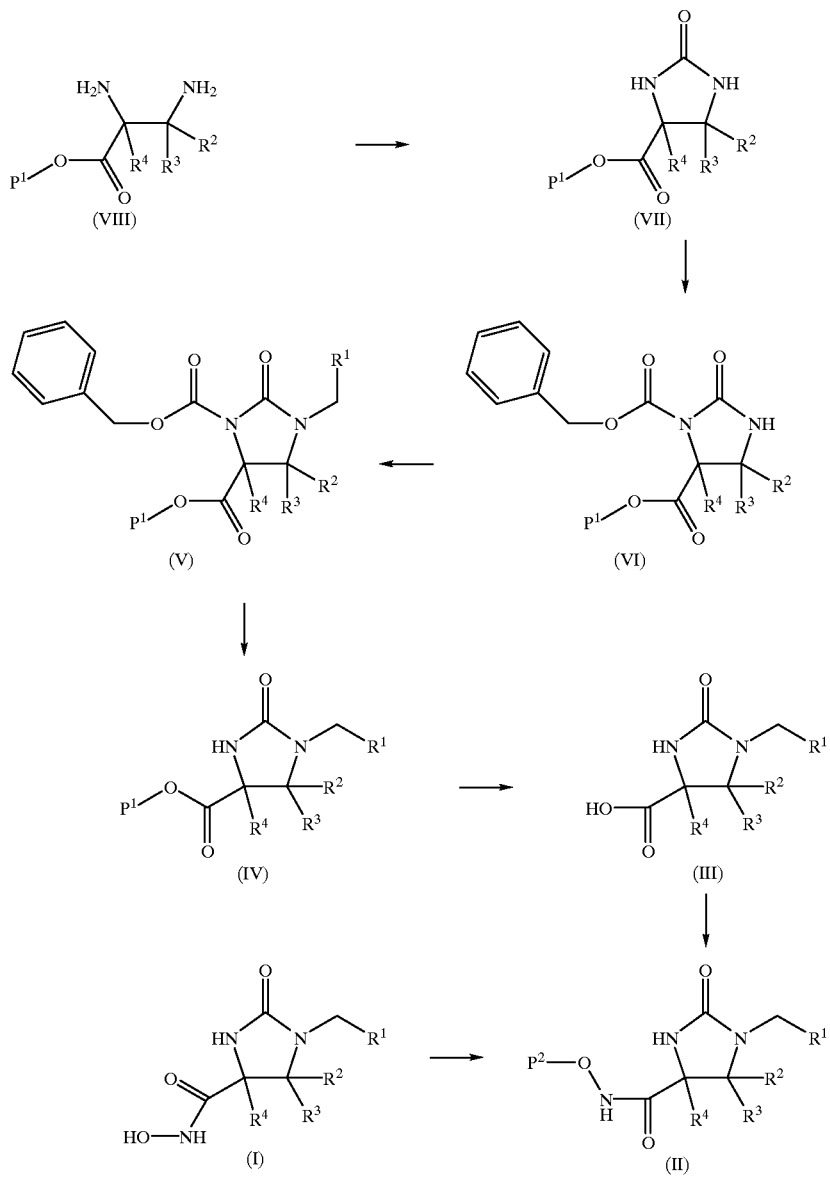

Scheme 1

General Reaction Conditions

Referring to Scheme 1, compounds of the formula I may be prepared from compounds of the formula II by removal of the hydroxyamide protecting group $p^2$ where $p^2$ can be solvent such as methylene chloride or chloroform, preferably methylene chloride, at a temperature from about 0° C. to about 50° C., preferably about 20° C. When $p^2$ is allyl, removal of the protecting group may be carried out by treatment with tributyltin hydride and acetic acid in the presence of catalytic bis(triphenylphosphine) palladium (II) chloride.

Referring to Scheme 1, compounds of the formula II may be prepared from carboxylic acids of the formula III by reaction with a hydroxylamine derivative of the formula $P^2ONH_2$ in the presence of an activating agent such as 1-(3-dimethylaminopropyl)-3-ethylcarbodiimide and 1-hydroxybenztriazole in an aprotic solvent, such as methylene chloride or N,N-dimethylformamide, preferably methylene chloride, The reaction is conducted at a temperature of about 0° C. to about 50° C., preferably about 20° C. The hydroxylamine of the formula $P^2ONH_2$ is preferably generated in situ from a salt form, such as the hydrochloride, in the presence of a base, such as triethylamine or diisopropylethylamine, preferably diisopropylethylamine.

The compounds of the formula III may be prepared from compounds of the formula IV by removal of the carboxylic acid protecting group $P^1$ where $P^1$ is methyl, ethyl or tert-butyl, preferably tert-butyl. When $P^1$ is methyl or ethyl, removal of the the protecting group $P^1$ is carried out by reaction with excess of a metal hydroxide, such as sodium hydroxide or lithium hydroxide, preferably lithium hydroxide, in a protic solvent, such as aqueous ethanol, at a temperature of about 0° C. to about 100° C., preferably about 20° C. In cases where the solubility of IV is limited, tetrahydrofuran may be added to the reaction mixture as a co-solvent. When $P^1$ is tert-butyl, removal of the protecting group $P^1$ is carried out by treatment with a strong acid such as hydrochloric acid or trifluoroacetic acid, preferably trifluoroacetic acid, in an inert solvent such as chloroform or methylene chloride, preferably methylene chloride. The reaction is carried out at a temperature of about 0° C. to about 50° C., preferably about 200° C.

The compounds of the formula IV may be prepared from compounds of the formula V by hydrogenation under an atmosphere of hydrogen in the presence of a catalyst in a reaction inert solvent. Suitable catalysts include palladium on carbon, palladium hydroxide on carbon or palladium black, preferably palladium on carbon. Suitable solvents include an alcohol such as ethanol, or methanol, preferably methanol. The aforesaid reaction may be performed at a pressure from about 1 to about 5 atmospheres, preferably about 3 atmospheres. Suitable temperatures for the aforesaid reaction range from about 20° C. (room temperature) to about 60° C., preferably about 20° C.

The compounds of formula V may be prepared from the compounds of formula VI by reaction with a base and an alkylating agent of the formula $R^1(CH_2)$—X, wherein X is a leaving group such as Br, I or para-toluenesulfonate. Suitable bases include potassium carbonate, cesium carbonate, potassium hexamethyldisilazide, or sodium hydride, preferably potassium carbonate. The reaction is stirred in a polar solvent, such as acetone, N,N-dimethylformamide, or N-methylpyrrolidin-2-one at a temperature from about 0° C. to about 50° C., preferably about 20° C.

The compounds of formula V wherein $R^4$ is $(C_1-C_6)$alkyl can be obtained via alkylation of compounds of the formula V wherein $R^4$ is hydrogen. The alkylation is carried out by reaction of an intermediate of formula V wherein $R^4$ is hydrogen with an alkyl halide of the formula $CH_3(CH_2)_nX$ wherein n is 0 to 5 and X is bromo or iodo. The aforesaid reaction is run in the presence of a hindered strong base such as lithium diisopropylamide or lithium hexamethyidisilazide in an inert solvent such as diethyl ether or tetrahydrofuran at a temperature from about −78° C. to about 0° C., preferably about −78° C.

The compounds of the formula VI can be prepared from compounds of the formula VII by reaction with benzyl chloroformate in the presence of a base such as triethylamine or diisopropylethylamine, preferably triethylamine and a catalytic amount of 4-dimethylaminopyridine. The aforesaid reaction is carried out in a solvent such as tetrahydrofuran, methylene chloride or chloroform, preferably methylene chloride, at a temperature from about 0° C. to about 20° C., preferably about 20° C.

The compounds of the formula VII may be obtained from diamino compounds of the formula VIII by reaction with phosgene, carbonyl diimidazole or triphosgene, preferably triphosgene in the presence of a base such as pyridine or triethylamine, preferably triethylamine. The aforesaid reaction is carried out in a solvent such as tetrahydrofuran, methylene chloride or chloroform, preferably tetrahydrofuran, at a temperature from about 0° C. to about 20° C., preferably about 20° C.

Compounds of formula VIII where $P^1$ is methyl or ethyl, $R^4$ is hydrogen, and $R^2$ and $R^3$ are independently $(C_1-C_6)$alkyl can be obtained from ketones of the formula $R^2R^3CO$ wherein $R^2$ and $R^3$ are independently $(C_1-C_6)$alkyl. Similarly, compounds of formula VIII where $P_1$ is methyl or ethyl, $R^4$ is hydrogen, and $R^2$ and $R^3$ taken together form a spiro ring of the formula

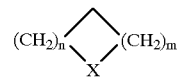

wherein X is a bond, $CH_2$, O, S, NH or $N(C_1-C_6)$alkyl, n is independently 1 or 2, and m is independently 1 or 2, can be prepared from cyclic ketones of the formula (IX) wherein X is a bond, $CH_2$, O, S, NH or $N(C_1-C_6)$alkyl, n is independently 1 or 2, and m is independently 1 or 2.

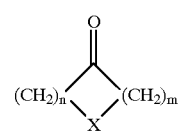

(IX)

The procedures are the same as those described by Schollkopf et al in the case where $R^2$ and $R^3$ are methyl (*Liebigs Ann. Chem.* 1973, 611 and *Liebigs Ann. Chem.* 1977, 1183).

Compounds of formula VIII wherin $P^1$ is methyl or ethyl, and $R^3$ and $R^4$ are hydrogen may be prepared from compounds of the formula X:

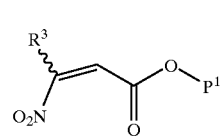

(X)

wherein $R^3$ is $(C_1-C_6)$alkyl. The procedures are the same as those described by Mohan et al in the case where $R^3$ is isopropyl (*J. Med. Chem.* 1991, 34, 2402). Several methods for preparing compounds of formula IX are known in the literature, for example Shin et al, *Bull. Chem. Soc. Jpn.* 1972, 45, 3595.

The compound of formula VI wherein $P^1$ is tert-butyl and $R^2$, $R^3$ and $R^4$ are hydrogen is known in the literature as the S enantiomer (Shiba et al. *Bull. Chem. Soc. Japan*, 1968, 41, 2748). The corresponding R enantiomer is prepared as described for the S enantiomer, using N-benzyloxycarbonyl-D-asparagine in place of N-benzyloxycarbonyl-L-asparagine as starting material.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

For administration to mammals, including humans, for the inhibition of matrix metalloproteinases, for inhibition of production of tumor necrosis factor (TNF) and, for example, for the inhibition of mammalian reprolysin (preferably inhibition of aggrecanase), a variety of a variety of conventional routes may be used including oral, parenteral (e g, intravenous, intramuscular or subcutaneous), buccal, anal and topical. In general, the compounds of the invention (hereinafter also known as the active compounds) will be administered at dosages between about 0.1 and 25 mg/kg body weight of the subject to be treated per day, preferably from about 0.3 to 5 mg/kg. Preferably the active compound will be administered orally or parenterally. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

The active compounds of the invention may also be formulated in rectal compositions such as suppositories or retention enemas, eg., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, eg., dichlorodifluoromethane, trichlorofluoromethane, dichlorotetrafluoroethane, carbon dioxide or other suitable gas. In the case of a pressurized aerosol, the dosage unit may be adetermined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

The ability of the compounds of formula I or their pharmaceutically acceptable salts (hereinafter also referred to as the compounds of the present invention) to inhibit metalloproteinases or mammalian reprolysin and, consequently, demonstrate their effectiveness for treating diseases characterized by metalloproteinase or the production of tumor necrosis factor is shown by the following in vitro assay tests.

BIOLOGICAL ASSAYS

Inhibition of Soluble TNF Production

The ability of the compounds or the pharmaceutically acceptable salts thereof to inhibit the cellular production/release of TNF and, consequently, demonstrate their effectiveness for treating diseases involving the dysregulated of TNF is shown by the following in vitro assay:

Method for the Evaluation of Recombinant TNFα Converting Enzyme Activity

1) Preparation of Recombinant TACE:

A DNA fragment coding for the signal sequence, pro-domain and catalytic domain of TACE (amino acids 1–473), was amplified by polymerase chain reaction using a human lung cDNA library as a template. The amplified fragment was cloned into pFastBac vector. The DNA sequence of the insert was confirmed for both the strands. A bacmid prepared using pFastBac in *E. coli* DH10Bac was transfected into SF9 insect cells. The virus particles were amplified to P1, P2, P3 stages. The P3 virus was infected into both Sf9 and High Five insect cells and grown at 27° C. for 48 hours. The medium was collected and used for assays and further purification.

2) Preparation of Fluorescent Quenched Substrate:

A model peptidic TNF-α substrate (LY-LeucineAlanineGlutamineAlanineValine-ArginineSerine-SerineLysine(CMTR)-Arginine (LY=Lucifer Yellow; CMTR=5-carboxytetramethyl Rhodamine)) was prepared and the concentration estimated by absorbance at 560 nm ($E_{560}$, 60,000 M-1CM-1) according to the method of Geoghegan, KF, "Improved method for converting an unmodified peptide to an energy-transfer substrate for a proteinase." *Bioconjugate Chem.* 7, 385–391 (1995). This peptide encompasses the cleavage cite on pro-TNF which is cleaved in vivo by TACE.

3) Enzyme Reaction.

The reaction, carried out in a 96 well plate (Dynatech), was comprised of 70 μl of buffer solution (25 mM Hepes-HCl, pH7.5, plus 20 uM $ZnCl_2$), 10 μl of 100 μM fluorescent quenched substrate, 10 μl of a DMSO (5%) solution of test compound, and an amount of r-TACE enzyme which will cause 50% cleavage in 60 minutes—in a total volume of 100 μl. The specificity of the enzyme cleavage at the amide bond between alanine and valine was verified by HPLC and mass spectrometry. Initial rates of cleavage were monitored by measuring the rate of increase in fluorescence at 530 nm (excitation at 409 nm) over 30 minutes. The experiment was controlled as follows: 1) for background fluorescence of substrate; 2) for fluorescence of fully cleaved substrate; 3) for fluorescence quenching or augmentation from solutions containing test compound.

Data was analyzed as follows. The rates from the non-test compound containing "control" reactions were averaged to establish the 100% value. The rate of reaction in the presence of test compound was compared to that in the absence of compound, and tabulated as "percent of non-test compound containing control. The results were plotted as "% of control" vs. the log of compound concentration and a half-maximal point or $IC_{50}$ value determined. The $IC_{50}$ for the above assay is a measure of the inhibition of the TNF-α proteolytic activity of TACE. Blockage of binding of TNF-α to TACE as used herein is as described in U.S. Pat. No. 5,830,742, issued Nov. 3, 1998.

Monocyte Assay

Human mononuclear cells were isolated from anti-coagulated human blood using a one-step Ficoll-hypaque separation technique. (2) The mononuclear cells were washed three times in Hanks balanced salt solution (HBSS) with divalent cations and resuspended to a density of $2 \times 10^6$/ml in HBSS containing 1% BSA. Differential counts determined using the Abbott Cell Dyn 3500 analyzer indicated that monocytes ranged from 17 to 24% of the total cells in these preparations.

180m of the cell suspension was aliquoted into flat bottom 96 well plates (Costar). Additions of compounds and LPS (100 ng/ml final concentration) gave a final volume of 200 μl. All conditions were performed in triplicate. After a four hour incubation at 37° C. in an humidified $CO_2$ incubator, plates were removed and centrifuged (10 minutes at approximately 250×g) and the supernatants removed and assayed for TNF-α using the R&D ELISA Kit.

MMP Assays

Collagenase-3 (matrix metalloproteinase-13) selective inhibitors as used herein refer to agents which exhibit at least a 100 fold selectivity for the inhibition of collagenase-3 enzyme activity over collagenase-1 enzyme activity and a potency of less than 100 nM as defined by the IC50 results from the MMP-13/MMP-1 fluorescence assays described below. Collagenase-3 selective inhibitors can be identified by screening the inhibitors of the present invention through the MMP-13/MMP-1 fluorescence assays described below and selecting those agents with MMP-13/MMP-1 inhibition $IC^{50}$ ratios of 100 or greater and potency of less than 100 nM.

Non-selective collagenase inhibitors as used herein refer to agents which exhibit less than a 100 fold selectivity for the inhibition of collagenase-3 enzyme activity over collagenase-1 enzyme activity or a potency of more than 100 nM as defined by the $IC_{50}$ results from the MMP-13/MMP-1 fluorescence assays described below.

The ability of collagenase inhibitors to inhibit collagenase activity is well known in the art. The following assays may be used to identify matrix metalloproteinase inhibitors.

Inhibition of Human Collagenase (MMP-1)

Human recombinant collagenase is activated with trypsin using the following ratio: 10 μg trypsin per 100 μg of collagenase. The trypsin and collagenase are incubated at room temperature for 10 minutes then a five fold excess (50 μg/10 μg trypsin) of soybean trypsin inhibitor is added.

10 mM stock solutions of inhibitors are made up in dimethyl sulfoxide and then diluted using the following Scheme:

10 mM→120 μM→12 μM→1.2 μM→0.12 μM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D1-D6 and blanks (no enzyme, no inhibitors) are set in wells D7-D12.

Collagenase is diluted to 400 ng/ml and 25 μl is then added to appropriate wells of the microfluor plate. Final concentration of collagenase in the assay is 100 ng/ml.

Substrate (DNP-Pro-Cha-Gly-Cys(Me)-His-Ala-Lys (NMA)-NH$_2$) is made as a 5 mM stock in dimethyl sulfoxide and then diluted to 20 mM in assay buffer. The assay is initiated by the addition of 50 μl substrate per well of the microfluor plate to give a final concentration of 10 μM.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration vs % control (inhibitor fluorescence divided by fluorescence of collagenase alone×100). $IC_{50}$'s are determined from the concentration of inhibitor that gives a signal that is 50% of the control.

If $IC_{50}$'s are reported to be <0.03 μM then the inhibitors are assayed at concentrations of 0.3 μM, 0.03 μM, 0.03 μM and 0.003 μM.

Inhibition of Gelatinase (MMP-2)

Inhibition of gelatinase activity is assayed using the Dnp-Pro-Cha-Gly-Cys(Me)-His-Ala-Lys(NMA)-NH$_2$ substrate (10 μM) under the same conditions as inhibition of human collagenase (MMP-1). 72 kD gelatinase is activated with 1 mM APMA (p-aminophenyl mercuric acetate) for 15 hours at 4° C. and is diluted to give a final concentration in the assay of 100 mg/ml. Inhibitors are diluted as for inhibition of human collagenase (MMP-1) to give final concentrations in the assay of 30 μM, 3 μM, 0.3 μM and 0.03 μM. Each concentration is done in triplicate.

Fluorescence readings (360 nm excitation, 460 emission) are taken at time zero and then at 20 minutes intervals for 4 hours.

$IC_{50}$'s are determined as per inhibition of human collagenase (MMP-1). If $IC_{50}$'s are reported to be less than 0.03 μM, then the inhibitors are assayed at final concentrations of 0.3 μM, 0.03 μM, 0.003 μM and 0.003 μM.

Inhibition of Stromelysin Activity (MMP-3)

Inhibition of stromelysin activity is based on a modified spectrophotometric assay described by Weingarten and Feder (Weingarten, H. and Feder, J., Spectrophotometric Assay for Vertebrate Collagenase, Anal. Biochem. 147, 437–440 (1985)). Hydrolysis of the thio peptolide substrate [Ac-Pro-Leu-Gly-SCH[CH$_2$CH(CH$_3$)$_2$]CO-Leu-Gly-OC$_2$H$_5$,] yields a mercaptan fragment that can be monitored in the presence of Ellman's reagent.

Human recombinant prostromelysin is activated with trypsin using a ratio of 1 μl of a 10 μmg/ml trypsin stock per 26 mg of stromelysin. The trypsin and stromelysin are incubated at 37° C. for 15 minutes followed by 10 μl of 10 μg/ml soybean trypsin inhibitor for 10 minutes at 37° C. for 10 minutes at 37° C. to quench trypsin activity.

Assays are conducted in a total volume of 250 ml of assay buffer (200 mM sodium chloride, 50 mM MES, and 10 mM calcium chloride, pH 6.0) in 96-well microliter plates. Activated stromelysin is diluted in assay buffer to 25 μg/ml. Ellman's reagent (3–Carboxy-4-nitrophenyl disulfide) is made as a 1M stock in dimethyl formamide and diluted to 5 mM in assay buffer with 50 ml per well yielding at 1 mM final concentration.

10 mM stock solutions of inhibitors are made in dimethyl sulfoxide and diluted serially in assay buffer such that addition of 50 μL to the appropriate wells yields final concentrations of 3 μM, 0.3 μM, 0.003 μM, and 0.0003 μM. All conditions are completed in triplicate.

A 300 mM dimethyl sulfoxide stock solution of the peptide substrate is diluted to 15 mM in assay buffer and the assay is initiated by addition of 50 μl to each well to give a final concentration of 3 mM substrate. Blanks consist of the peptide substrate and Ellman's reagent without the enzyme. Product formation was monitored at 405 nm with a Molecular Devices UVmax plate reader.

$IC_{50}$ values were determined in the same manner as for collagenase.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 pM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 μM, 3 μM, 0.3 μM, and 0.03 μM.

Substrate (Dnp-Pro-Cha-Gly-Cys(Me)-His-Aia-Lys (NMA)-NH$_2$) is prepared as for inhibition of human collagenase (MMP-1) and 50 ml is added to each well to give a final assay concentration of 10 μM. Fluorescence readings (360 nM excitation; 450 emission) are taken at time 0 and every 5 minutes for 1 hour.

Positive controls consist of enzyme and substrate with no inhibitor and blanks consist of substrate only.

$IC_{50}$'s are determined as per inhibition of human collagenase (MMP-1). If IC50's are reported to be less than 0.03 μM, inhibitors are then assayed at final concentrations of 0.3 μM, 0.03 μM, 0.003 μM and 0.0003 μM.

Collagen film MMP-13 Assay

Rat type I collagen is radiolabeled with $^{14}C$ acetic anhydride (T. E. Cawston and A. J. Barrett, Anal. Biochem., 99, 340–345 (1979)) and used to prepare 96 well plates containing radiolabeled collagen films (Barbara Johnson-Wint, Anal. Biochem., 104, 175–181 (1980)). When a solution containing collagenase is added to the well, the enzyme cleaves the insoluble collagen which unwinds and is thus solubilized. Collagenase activity is directly proportional to the amount of collagen solubilized, determined by the proportion of radioactivity released into the supernatant as measured in a standard scintillation counter. Collagenase inhibitors are, therefore, compounds which reduce the radioactive counts released with respect to the controls with no inhibitor present. One specific embodiment of this assay is described in detail below.

For determining the selectivity of compounds for MMP-13 versus MMP-1 using collagen as a substrate, the following procedure is used. Recombinant human proMMP-13 or proMMP-1 is activated according to the procedures outlined above. The activated MMP-13 or MMP-1 is diluted to 0.6 ug/ml with buffer (50 mM Tris pH 7.5, 150 mM NaCl, 10 mM $CaCl_2$, 1 uM $ZnCl_2$, 0.05% Brij-35, 0.02% sodium azide).

Stock solutions of test compound (10 mM) in dimethylsulfoxide are prepared. Dilutions of the test compounds in the Tris buffer, above, are made to 0.2, 2.0, 20, 200, 2000 and 20000 nM.

100 $\mu$l of appropriate drug dilution and 100 $\mu$l of diluted enzyme are pipetted into wells of a 96 well plate containing collagen films labeled with $^{14}$C-collagen. The final enzyme concentration is 0.3 $\mu$g/ml while the final drug concentration is 0.1, 1.0, 10, 100, 1000 nM. Each drug concentration and control is analyzed in triplicate. Triplicate controls are also run for the conditions in which no enzyme is present and for enzyme in the absence of any compound.

The plates are incubated at 37° C. for a time period such that around 30–50% of the available collagen is solubilized—determined by counting additional control wells at various time points. In most cases around 9 hours of incubation are required. When the assay has progressed sufficiently, the supernatant from each well is removed and counted in a scintillation counter. The background counts (determined by the counts in the wells with no enzyme) are subtracted from each sample and the % release calculated in relation to the wells with enzyme only and no inhibitor. The triplicate values for each point are averaged and the data graphed as percent release versus drug concentration. $IC_{50}$'s are determined from the point at which 50% inhibition of release of radiolabeled collagen is obtained.

To determine the identity of the active collagenases in cartilage conditioned medium, assays were carried out using collagen as a substrate, cartilage conditioned medium containing collagenase activity and inhibitors of varying selectivity. The cartilage conditioned medium was collected during the time at which collagen degradation was occurring and thus is representative of the collagenases responsible for the collagen breakdown. Assays were carried out as outlined above except that instead of using recombinant MMP-13 or recombinant MMP-1, cartilage conditioned medium was the enzyme source.

IL-1 Induced Cartilage Collagen Degradation from Bovine Nasal Cartilage

This assay uses bovine nasal cartilage explants which are commonly used to test the efficacy of various compounds to inhibit either IL-1 induced proteoglycan degradation or IL-1 induced collagen degradation. Bovine nasal cartilage is a tissue that is very similar to articular cartilage, i.e. chondrocytes surrounded by a matrix that is primarily type II collagen and aggrecan. The tissue is used because it: (1) is very similar to articular cartilage, (2) is readily available, (3) is relatively homogeneous, and (4) degrades with predictable kinetics after IL-1 stimulation.

Two variations of this assay have been used to assay compounds. Both variations give similar data. The two variations are described below:

Variation 1

Three plugs of bovine nasal cartilage (approximately 2 mm diameter×1.5 mm long) are placed into each well of a 24 well tissue culture plate. One ml of serumless medium is then added to each well. Compounds are prepared as 10 mM stock solutions in DMSO and then diluted appropriately in serumless medium to final concentrations, eg., 50, 500 and 5000 nM. Each concentration is assayed in triplicate.

Human recombinant IL-1$\alpha$ (5ng/mL) (IL-1) is added to triplicate control wells and to each well containing drug. Triplicate control wells are also set up in which neither drug nor IL-1 are added. The medium is removed and fresh medium containing IL-1 and the appropriate drug concentrations is added on days 6, 12, 18 and 24 or every 3–4 days if necessary. The media removed at each time point is stored at −20° C. for later analysis. When the cartilage in the IL-1 alone wells has almost completely resorbed (about day 21), the experiment is terminated. The medium, is removed and stored. Aliquots (100 ul) from each well at each time point are pooled, digested with papain and then analyzed for hydroxyproline content. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot.

Variation 2

The experimental set-up is the same as outlined above in Variation 1, until day 12. On day 12, the conditioned medium from each well is removed and frozen. Then one ml of phosphate buffered saline (PBS) containing 0.5 $\mu$g/ml trypsin is added to each well and incubation continued for a further 48 hours at 37° C. After 48 hours incubation in trypsin, the PBS solution is removed. Aliquots (50 $\mu$l) of the PBS/trypsin solution and the previous two time points (days 6 and 12) are pooled, hydrolyzed and hydroxyproline content determined. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot. In this variation, the time course of the experiment is shortened considerably. The addition of trypsin for 48 hours after 12 days of IL-1 stimulation likely releases any type II collagen that has been damaged by collagenase activity but not yet released from the cartilage matrix. In the absence of IL-1 stimulation, trypsin treatment produces only low background levels of collagen degradation in the cartilage explants.

Inhibition of Human 92 kD Gelatinase (MMP-9)

Inhibition of 92 kD gelatinase (MMP-9) activity is assayed using the Mca-Pro-Leu-Gly-Leu-Dpa-Ala-Arg-NH$_2$ substrate (10 $\mu$M) under similar conditions as described above for the inhibition of human collagenase (MMP-1).

Human recombinant 92 kD gelatinase (MMP-9, gelatinase B) is activated for 2 hours with 1mM p-aminophenylmercuric acetate (from a freshly prepared 100 mM stock in 0.2 N NaOH) at 37 ° C.

10 mM dimethylsulfoxide stock solutions of inhibitors are diluted serially in assay buffer (50 mM TRIS, pH 7.5, 200 mM NaCl, 5 mM CaCl$_2$, 20 $\mu$M ZnCl$_2$, 0.02% BRIJ-35 (vol./vol.)) using the following scheme:

10 mM→120 $\mu$M→12 $\mu$M→1.2 $\mu$M→0.12 $\mu$M

Further dilutions are made as necessary following this same scheme. A minimum of four inhibitor concentrations for each compound are performed in each assay. 25 $\mu$L of each concentration is then added to triplicate wells of a black 96 well U-bottomed microfluor plate. As the final assay volume is 100 µL, final concentrations of inhibitor are the result of a further 1:4 dilution (i.e. 30 µM→3 µM→0.3 µM→0.03 µM, etc.). A blank (no enzyme, no inhibitor) and a positive enzyme control (with enzyme, no inhibitor) are also prepared in triplicate.

Activated enzyme is diluted to 100 ng/mL in assay buffer, 25 µL per well is added to appropriate wells of the microplate. Final enzyme concentration in the assay is 25 ng/mL (0.27 nM).

A five mM dimethylsulfoxide stock solution of substrate (Mca-Pro-Leu-Gly-Leu-Dpa-Ala-Arg-$NH_2$) is diluted in assay buffer to 20 µM. The assay is initiated by addition of 50 µL of diluted substrate yielding a final assay concentration of 10 JAM substrate. A 0 time fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The 0 time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Aggrecanase Assay

Primary porcine chondrocytes from articular joint cartilage are isolated by sequential trypsin and collagenase digestion followed by collagenase digestion overnight and are plated at 2×10$^5$ cells per well into 48 well plates with 5 µCi /ml $^{35}$S (1000 Ci/mmol) sulphur in type I collagen coated plates. Cells are allowed to incorporate label into their proteoglycan matrix (approximately 1 week) at 37° C., under an atmosphere of 5% $CO_2$.

The night before initiating the assay, chondrocyte monolayers are washed two times in DMEM/1% PSF/G and then allowed to incubate in fresh DMEM /1% FBS overnight.

The following morning chondrocytes are washed once in DMEM/1%PSF/G. The final wash is allowed to sit on the plates in the incubator while making dilutions.

| | |
|---|---|
| Control Media | DMEM alone (control media) |
| IL-1 Media | DMEM + IL-1 (5 ng/ml) |
| Drug Dilutions | Make all compounds stocks at 10 mM in DMSO. Make a 100 uM stock of each compound in DMEM in 96 well plate. Store in freezer overnight. The next day perform serial dilutions in DMEM with IL-1 to 5 uM, 500 nM, and 50 nM. Aspirate final wash from wells and add 50 ul of compound from above dilutions to 450 ul of IL-1 media in appropriate wells of the 48 well plates. Final compound concentrations equal 500 nM, 50 nM, and 5 nM. All samples completed in triplicate with Control and IL-1 alone samples on each plate. |

Plates are labeled and only the interior 24 wells of the plate are used. On one of the plates, several columns are designated as IL-1 (no drug) and Control (no IL-1, no drug). These control columns are periodically counted to monitor 35S-proteoglycan release. Control and IL-1 media are added to wells (450 ul) followed by compound (50 ul) so as to initiate the assay. Plates are incubated at 37° C., with a 5% $CO_2$ atmosphere.

At 40–50% release (when CPM from IL-1 media is 4–5 times control media) as assessed by liquid scintillation counting (LSC) of media samples, the assay is terminated (9–12 hours). Media is removed from all wells and placed in scintillation tubes. Scintillate is added and radioactive counts are acquired (LSC). To solubilize cell layers, 500 ul of papain digestion buffer (0.2 M Tris, pH 7.0, 5 mM EDTA, 5 mM DTT, and 1 mg/ml papain) is added to each well. Plates with digestion solution are incubated at 60° C. overnight. The cell layer is removed from the plates the next day and placed in scintillation tubes. Scintillate is then added, and samples counted (LSC).

The percent of released counts from the total present in each well is determined. Averages of the triplicates are made with control background subtracted from each well. The percent of compound inhibition is based on IL-1 samples as 0% inhibition (100% of total counts).

The compounds of the present invention that were tested had $IC_{50}$ of less than 1 µM, preferably less than 50nM in at least one of the assays described above. The compounds of the present invention also possess differential activity (i.e. are selective for) for one or more reprolysin or MMP. Selectivity as used herein refers to the ratio of the $IC_{50}$ inhibitory results from two or more of the above protocols. Compounds of the invention which are selective possess a ratio of at least 10. The compounds of the invention possessing the potency or selectivity desired can be identified by assaying a compound (preferably a small molecule, more preferably a hydroxamic acid, most preferably a compound of formula I) according to the protocols described above and determining the $IC_{50}$ and selectivity ratios.

One group of preferred compounds (more preferably compounds of the formula I) that can be identified by the methods of the present invention include those inhibitors that possess selective activity against MMP-13 over MMP-1, (preferably an $IC_{50}$ of less than 500 nM, more preferably 100 nM, most preferably 50 nM) for MMP-13 with a selectivity of at least 10 fold, preferably 40 fold, higher for MMP-13 over MMP-1.

PREPARATION OF COMPOUNDS

The following Examples illustrate the preparation of the compounds of the present invention. Melting points are uncorrected. NMR data are reported in parts per million (δ). Commercial reagents were utilized without further purification. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields.

Example 1

(4R)-1-[4-(4-Fluorophenoxy)benzyl]-2-oxo-imidazolidine-4-carboxylic Acid Hydroxyamide a) (4R)-3-[4-(4-Fluorophenoxy)benzyl]-2-oxo-imidazolidine-1,5-dicarboxylic Acid 1-Benzyl Ester 5-Tert-butyl Ester.

To a solution of (4R)-oxo-imidazolidine-1,5-dicarboxylic acid 1-benzyl ester 5-tert-butyl ester (650 mg, 2.0 mmol) in acetone (10 mL) was added powdered $K_2CO_3$ (550 mg, ) and 4-(4-fluorophenoxy)benzylbromide (1.85 g, 6.6 mmol).

The reaction mixture was stirred at room temperature for 6 days and then the Solvent was evaporated. The residue was taken up in ethyl acetate and washed with water and brine. After drying over $MgSO_4$, the solvent was evaporated. The title compound (820 mg, 78%) was isolated from the residue by chromatography on silica gel eluting with chloroform.

b) (4R)-1-[4-(4-Fluorophenoxy)benzyl]-2-oxo-imidazolidine-4-carboxylic Acid Tert-butyl Ester A solution of (4R)-3-[4-(4-fluorophenoxy)benzyl]-2-oxo-imidazolidine-1,5-dicarboxylic acid 1-benzyl ester 5-tert-butyl ester (1.1 g, 2.1 mmol) in methanol (100 mL) was hydrogenated over 10% Pd on carbon (110 mg) at 3 atmospheres pressure for 6 hours. After removal of the catalyst by filtration through a 0.45 μm pore nylon filter, the solvent was evaporated to afford the title compound (810 mg, 100%) as a yellow solid.

c) (4R)-1-[4-(4-Fluorophenoxy)benzyl]-2-oxo-imidazolidine-4-carboxylic Acid

A solution of (4R)-1-[4-(4-fluorophenoxy)benzyl]-2-oxo-imidazolidine-4-carboxylic acid tert-butyl ester (810 mg, 1.56 mmol) in $CH_2Cl_2$ (8 mL) was treated with trifluoroacetic acid (8 mL). The reaction mixture was stirred at room temperature for 2.5 hours and concentrated to leave an oil. The title compound, a white solid (297 mg, 58%), was collected by filtration, after triturating the oil with a mixture of warm diethyl ether and hexane.

d) (4R)-1-[4-(4-Fluorophenoxy)benzyl]-2-oxo-imidazolidine-4-carboxylic Acid(2-trimethylsilanyleth oxy)amide.

To a solution of (4R)-1 -[4-(4-fluorophenoxy)benzyl]-2-oxo-imidazolidine-4-carboxylic acid (120 mg, 0.36 mmol) in methylene chloride (5 mL) were added sequentially 1-hydroxybenztria zole (73 mg, 0.54 mmol), diisopropyl-ethylamine (0.13 mL, 0.75 mmol), O-(2-trimethylsilylethyl) hydroxylamine hydrochloride (92 mg, 0.54 mmol) and 1-[3-(dimethylamino)propyl]-3-ethylcarbodiimide hydrochloride (104 mg, 0.54 mmol). The reaction mixture was stirred at room temperature for 16 hours and was then diluted with methylene chloride and water. The organic phase was washed successively with aqueous 1M HCl solution, water, aqueous saturated $NaHCO_3$ solution and brine. After drying over $MgSO_4$, the solution was concentrated to an oil. The title compound, an oil (85 mg, 53%), was isolated by chromatography on silica gel eluting with ethyl acetate.

e) (4R)-1 -[4-(4-Fluorophenoxy)benzyl]-2-oxo-imidazolidine-4-carboxylic Acid Hydroxyamide To a solution of (4R)-1-[4-(4-fluorophenoxy)benzyl]-2-oxo-imidazolidine-4-carboxylic acid (2-trimethylsilanylethoxy)amide (85 mg, 0. 19 mmol) in methylene chloride (5 mL) was added boron trifluoride etherate (0.073 mL, 0.58 mmol). The reaction mixture was stirred at room temperature for 1.5 hours and then quenched by addition of aqueous saturated $NH_4Cl$ solution. The mixture was diluted with water and ethyl acetate and the organic phase was washed with brine, dried over $MgSO_4$ and concentrated to a white solid. The title compound (31 mg, 47%) was isolated by recrystallization from a mixture of ethyl acetate and methanol.

$^1H$ NMR (DMSO-$d_6$): δ 10.63 (br s, 1 H), 8.93 (br s, 1 H), 7.23–7.17 (m, 4 H), 7.05–7.01 (m, 2 H), 6.92 (d, J=8.7 Hz, 2 H), 6.76 (s, 1 H), 4.22 (d, J=15.2 Hz, 1 H), 4.15 (d, J=15.2 Hz, 1 H), 3.92–3.89 (m, 1 H), 3.40 (apparent t, J=9.1 Hz, 1H), 3.15–3.12 (m, 1 H), MS m/z 344 (M-1). Analysis calculated for $C_{19}H_{16}FN_3O_4$: C, 59.13; H, 4.67; 12.17. Found: C, 58.98; H, 4.83; N, 12.10.

Example 2

(4R)-1-[4-(Naphthalen-1-yloxy)benzyl]-2-oxo-imidazolidine-4-carboxylic Acid Hydroxyamide MS m/z 376 (M-1). Analysis calculated for $C_{21}H_{19}N_3O_4$: C, 66.83; H, 5.07; N, 11.13. Found: C, 66.75; H, 5.30; N, 11.13.

Example 3

(4R)-1-[4-(Naphthalen-2-yloxy)benzyl]-2-oxo-imidazolidine-4-carboxylic Acid Hydroxyamide MS m/z 376 (M-1). Analysis calculated for $C_{21}H_{19}N_3O_4$+0.5 $H_2O$: C, 65.28; H, 5.22; N 10.87. Found: C, 65.01; H, 5.12; N, 11.28.

Example 4

(4R)-1-(4-Methoxybenzyl)-2-oxo-imidazolidine-4-carboxylic Acid Hydroxyamide

M.p. 130–133 C. MS m/z 264 (M-1). Analysis calculated for $C_{12}H_{15}N_3O_4$: C, 54.33; H, 5.70; 15.84. Found: C, 54.24; H, 51.77; N, 15.62.

Example 5

(4R)-1-[3-(4-Fluorophenoxy)benzyl]-2-oxo-imidazolidine-4-carboxylic Acid Hydroxyamide MS m/z 344 (M-1). Analysis calculated for $C_{19}H_{16}FN_3O_4$: C, 59.13; H, 4.67; 12.17. Found: C, 59.24; H, 4.60; N, 12.42.

Example 6

(4R)-1-Naphthalen-2-ylmethyl-2-oxo-imidazolidine-4-carboxylic Acid Hydroxyamide

MS m/z 284 (M-1). Analysis calculated for $C_{15}H_{15}N_3O_3$: C, 63.15; H, 5.30; 14.73. Found: C, 62.82; H, 5.32; N, 14.49.

Example 7

(4R)-1-(4'-Fluorobiphenyl-4-ylmethyl)-2-oxo-imidazolidine-4-carboxylic Acid Hydroxyamide MS m/z 328 (M-1). Analysis calculated for $C_{17}H_{16}FN_3O_3$+0.5 $H_2O$: C, 60.35; H, 5.06; 12.42. Found: C, 60.43; H, 4.99; N, 12.83.

Example 8

(4R)-1-(4-Benzyloxybenzyl)-2-oxo-imidazolidine-4-carboxylic Acid Hydroxyamide

MS m/z 340 (M-1). Analysis calculated for $C_{18}H_{19}N_3O_4$: C, 63.33; H, 5.61; 12.31. Found: C, 63.13; H, 5.62; N, 12.28.

Example 9

(4R)-1-[4-(2-Chloro-4-fluorobenzyloxy)benzyl]-2-oxo-imidazolidine-4-carboxylic Acid Hydroxyamide MS m/z 392, 394 (M-1). Analysis calculated for $C_{18}H_{17}ClFN_3O_4$+0.5 $H_2O$: C, 53.67; H 4.50; 10.43. Found: C, 53.78; H, 4.51; N, 10.15.

What is claimed is:

1. A compound according to formula (1)

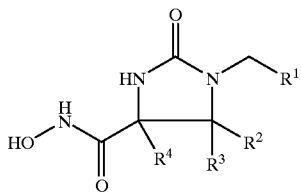

or a pharmaceutically acceptable salt or solvate thereof, wherein $R^1$ is $(C_6-C_{10})$aryl, $(C_6-C_{10})$aryl$(C_1-C_6)$alkyl, $(C_6-C_{10})$aryl$(C_6-C_{10})$aryl, $(C_6-C_{10})$aryloxy$(C_6-C_{10})$aryl, $(C_6-C_{10})$aryloxy$(C_1-C_6)$alkyl, $(C_6-C_{10})$aryl$(C_1-C_6)$alkyl $(C_6-C_{10})$aryl, $(C_6-C_{10})$aryl$(C_1-C_6)$alkoxy $(C_6-C_{10})$aryl, $(C_6-C_{10})$aryloxy$(C_1-C_6)$alkyl$(C_6-C_{10})$aryl, $(C_6-C_{10})$aryl$(C_6-C_{10})_{aryl(C_1}-C_6)$alkyl, or $(C_6-C_{10})$aryl$(C_1-C_6)$alkoxy$(C_1-C_6)$alkyl, wherein, independently, each of the ring carbon atoms of said $(C_6-C_{10})$aryl moieties that is capable of forming an additional bond is optionally substituted by a group selected from fluoro, chloro, bromo, $(C_1-C_6)$alkyl, $(C_1-C_6)$alkoxy, and perfluoro$(C_1-C_3)$alkyl, and perfluoro$(C_1-C_3)$alkoxy;

$R^2$ and $R^3$ are each independently selected from hydrogen and $(C_1-C_6)$alkyl, and $R^4$ is hydrogen or $(C_1-C_6)$alkyl.

2. A compound according to claim 1 of the formula (I')

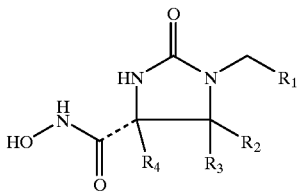

3. A compound according to claim 1 wherein $R^2$, $R^3$ and $R^4$ are hydrogen.

4. A compound according to claim 1 wherein $R^4$ is hydrogen.

5. A compound according to claim 1 wherein $R^4$ is $(C_1-C_6)$alkyl.

6. A compound according to claim 1 wherein $R^2$ and $R^3$ are hydrogen.

7. A compound according to claim 1 wherein $R^2$ and $R^3$ are $(C_1-C_6)$alkyl such that $R^2$ is the same as $R^3$.

8. A compound according to claim 1 wherein $R^1$ is selected from the group consisting of $(C_6-C_{10})$aryl, $(C_6-C_{10})$aryloxy$(C_6-C_{10})$aryl, $(C_6-C_{10})$aryl$(C_6-C_{10})$aryl, and $(C_6-C_{10})$aryl$(C_1-C_6)$alkoxy$(C_6-C_{10})$aryl.

9. A compound according to claim 1 wherein $R^1$ is selected from the group consisting of 4-[$(C_6-C_{10})$aryl]phenyl, 4-[$(C_6-C_{10})$aryloxy]phenyl and 4-[$(C_6-C_{10})$aryl$(C_1-C_6)$alkoxy]phenyl.

10. A compound according to claim 1 wherein $R^1$ is 4-(4-fluorophenoxy)phenyl.

11. A compound according to claim 1 wherein $R^1$ is 4-(4-chlorophenoxy)phenyl.

12. A compound according to claim 1, wherein $R^1$ is 4-(naphthalen-2-yloxy)phenyl.

13. A compound according to claim 3, wherein $R^1$ is selected from the group consisting of $(C_6-C_{10})$aryl, $(C_6-C_{10})$aryloxy$(C_6-C_{10})$aryl, $(C_6-C_{10})$aryl$(C_6-C_{10})$aryl, and $(C_6-C_{10})$aryl$(C_1-C_6)$alkoxy $(C_6-C_6)$aryl.

14. A compound according to claim 4, wherein $R^1$ it selected from the group consisting of $(C_6-C_{10})$aryl, $(C_6-C_{10})$aryloxy$(C_6-C_{10})$aryl, $(C_6-C_{10})$aryl$(C_6-C_{10})$aryl, and $(C_6-C_{10})$aryl$(C_1-C_6)$alkoxy$(_6-C_{10})$aryl.

15. A compound according to claim 5, wherein $R^1$ is-selected from the group consisting of $(C_6-C_{10})$aryl, $(C_6-C_{10})$aryloxy$(C_6-C_{10})$aryl, $(C_6-C_{10})$aryl $(C_6-C_{10})$aryl, and $(_6-C_{10})$aryl$(C_1-C_6)$alkoxy$(C_6-C_{10})$aryl.

16. A compound according to claim 6, wherein $R^1$ is, selected from the group consisting of $(C_6-C_{10})$aryl, $(C_6-C_{10})$aryloxy$(C_6-C_{10})$aryl, $(C_6-C_{10})$aryl$(C_6-C_{10})$aryl, and $(C_6-C_{10})$aryl$(C_1-C_6)$aryloxy$(C_6-C_{10})$aryl.

17. A compound according to claim 7, wherein $R^1$ is selected from the group consisting of $(C_6-C_{10})$aryl, $(C_6-C_{10})$aryloxy$(C_6-C_{10})$aryl, $(C_6-C_{10})$aryl$(C_6-C_{10})$aryl, and $(C_6-C_{10})$aryl$(C_1-C_6)$alkoxy$(C_6-C_{10})$aryl.

18. A compound according to claim 1 selected from the group consisting of:

(4R)-1-[4-(4-Fluorophenoxy)benzyl]-2-oxo-imidazolidine-4-carboxylic acid hydroxyamide;

(4R)-1-[4-(Naphthalen-1-yloxy)benzyl]-2-oxo-imidazolidine-4-carboxylic acid hydroxyamide;

(4R)-1-[4-(Naphthalen-2-yloxy)benzyl]-2-oxo-imidazolidine-4-carboxylic acid hydroxyamide;

(4R)-1-(4-Methoxybenzyl)-2-oxo-imidazolidine-4-carboxylic acid hydroxyamide;

(4R)-1-[3-(4-Fluorophenoxy)benzyl]-2-oxo-imidazolidine-4-carboxylic acid hydroxyamide;

(4R)-1-Naphthalen-2-ylmethyl-2-oxo-imidazolidine-4-carboxylic acid hydroxyamide;

(4R)-1-(4-Fluorobiphenyl-4-ylmethyl)-2-oxo-imidazolidine-4-carboxylic acid hydroxyamide;

(4R)-1-(4-Benzyloxybenzyl)-2-oxo-imidazolidine-4-carboxylic acid hydroxyamide; and (4R)-1-[4-(2-Chloro-4-florobenzyloxy)benzyl]-2-oxo-imid azolidine-4-carboxylic acid hydroxyamide.

19. A compound according to claim 1 selected from the group consisting of (4R)-1-[4-(4-Chlorophenoxy)benzyl]-2-oxo-imidazolidine4carboxylic acid hydroxyamide;

(4R)-1-[4-(4-Fluorophenoxy)benzyl]-5,5dimethyl-2-oxo-imidazolidinre-4-carboxylic acid hydroxyamide;

(4R)-1-[4-(4-Chlorophenoxy)benzyl]-5,5-dimethyl-2oxo-imidazolidine-4-carboxylic acid hydroxyamide;

(4R)-1-[4-(4-Fluorophenoxy)benzyl]methyl-2-oxo-imidazolidine-4-carboxylic acid hydroxyamide;

(4R)-1-[4-(4-Chlorophenoxy)benzyl]-4-methyl-2oxo-imidazolidine-4-carboxylic acid hydroxyamide;

(4R)-1-[4(4-Fluorophenoxy)benzyl]-4,5,5trimethyl-2-oxo-imidazolidine-4 carboxylic acid hydroxyamide;

(4R)-1-[4-(4-Chlorophenoxy)benzyl]-4,5,5-trimethyl-2-oxo-imidazolidine-4-carboxylic acid hydroxyamide;

(4R)-4-Methyl-1-[4(naphthalen-2-yloxy)benzyl]-2-oxo imidazolidin-4-carboxylic acid hydroxyamide; and (4R)-5,5-Dimethyl-1-[4-(naphthalen-2-yloxy)benzyl]-2-oxo-imidazolidine-4-carboxylic acid hydroxyamide.

20. A pharmaceutical composition for the treatment of a condition selected from the group consisting of osteoarthritis, rheumatoid arthritis, cancer, and congestive heart failure in a mammal, comprising an amount of a compound of claim 1 effective in such treatment, and a pharmaceutically acceptable carrier.

21. A method for treating a condition selected from the group consisting of osteoarthritis, rheumatoid arthritis, cancer, and congestive heart failure in a mammal, comprising administering to said mammal an amount of a compound of claim 1, effective in treating such a condition.

22. A method for the inhibition of matrix metalloproteinases in a mammal, comprising administering to said mammal an effective amount of a compound of claim 1.

23. A method for the inhibition of a mammalian reprolysin in a mammal, comprising administering to said mammal an effective amount of a compound of claim 1.

24. The pharmaceutical composition of claim 20 wherein said mammal is a human.

25. The method of claim 21 wherein said mammal is a human.

26. The method of claim 22 wherein said mammal is a human.

27. The method of claim 23 wherein said mammal is a human.

\* \* \* \* \*